United States Patent
Bryne

Patent Number: 5,222,999
Date of Patent: Jun. 29, 1993

[54] LIQUIFIED NITROGEN THERMAL CHECKING OF ELECTRONIC CIRCUITRY

[75] Inventor: Michael D. Bryne, Tolland, Conn.

[73] Assignee: Brymill Corporation, Vernon, Conn.

[21] Appl. No.: 963,232

[22] Filed: Oct. 19, 1992

Related U.S. Application Data

[63] Continuation of Ser. No. 835,117, Feb. 14, 1992, abandoned, which is a continuation of Ser. No. 380,219, Jul. 14, 1989, abandoned.

[51] Int. Cl.$^5$ .................. G01N 25/72; G01R 31/02
[52] U.S. Cl. .......................................... 374/5; 62/293; 324/158 F; 374/57
[58] Field of Search ............... 374/5, 45, 163, 57; 62/51.2; 606/23; 165/161; 324/158 F

[56] References Cited

U.S. PATENT DOCUMENTS

| | | | |
|---|---|---|---|
| 2,643,282 | 6/1953 | Greene | 62/259.2 X |
| 3,483,721 | 12/1969 | Apple et al. | 374/5 X |
| 3,710,251 | 1/1973 | Hagge et al. | 324/158 F |
| 3,782,386 | 1/1974 | Barger et al. | 62/293 X |
| 3,934,451 | 1/1976 | Bristoll et al. | 374/5 |
| 3,993,075 | 11/1971 | Lisenbee et al. | 606/26 X |
| 4,015,606 | 4/1977 | Mitchiner et al. | 62/293 X |
| 4,072,152 | 2/1978 | Linehan | 606/23 |
| 4,269,390 | 5/1981 | Bryne | 251/254 |
| 4,426,619 | 1/1984 | Demand | 324/158 F X |
| 4,487,253 | 12/1984 | Malek et al. | 165/179 X |
| 4,503,335 | 3/1985 | Takakashi | 324/158 F X |
| 4,787,752 | 11/1988 | Fraser et al. | 324/158 F X |
| 4,831,846 | 5/1989 | Sungaila | 606/22 X |
| 4,838,041 | 6/1989 | Bellows et al. | 62/293 X |
| 4,872,762 | 10/1989 | Koshihara et al. | 374/5 |
| 4,934,151 | 6/1990 | Shima | 62/64 |
| 4,954,774 | 9/1990 | Binet | 324/158 P X |
| 5,099,908 | 3/1992 | Taraci et al. | 361/385 X |

OTHER PUBLICATIONS

"Physical Constants" of Nitrogen in the CRC Handbook of Chemistry & Physics Robert C. Weast, et al, Editors p. B-103 1981.

"Device for Obtaining Temperatures of 4.2°-300° K. with Considerable Heat Flow Into Specimen", V I. Silaev et al. Instrument & Exp Tech. (USA), vol. 20, No. 3 PE2, pp. 864-865, (May-Jun. 1977, Publ. Dec. 1977).

"Close-Cycle Liquid Nitrogen Refrigeration System for Low-Temperature Computer Operation", V. L. Rideout, IBM Technical Disc. Bulletin, vol. 18, No. 4, Sep. 1975, (pp. 1226-1229).

*Primary Examiner*—Daniel M. Yasich
*Attorney, Agent, or Firm*—M. P. Williams

[57] ABSTRACT

Electronic circuitry 22, 24, 26 is thermally checked by cooling with liquified nitrogen from a cryogenic delivery unit 19, directly by means of a stream 10 or a spray 28 delivered through an aperture 11, 30 of the delivery unit 19 spaced from the surface of the circuitry.

11 Claims, 1 Drawing Sheet

LIQUIFIED NITROGEN THERMAL CHECKING OF ELECTRONIC CIRCUITRY

This is a continuation of application Ser. No. 07/835,117, filed Feb. 14, 1992, now abandoned, which in turn is a continuation of application Ser. No. 07/380,219, filed Jul. 14, 1989, now abandoned.

TECHNICAL FIELD

This invention relates to thermal checking of electronic circuitry, and more particularly, to checking electronic circuitry by means of liquified nitrogen.

BACKGROUND ART

It is common practice to utilize thermal checking to identify specific failed components in electronic circuitry, and to ensure operation at specific, cold temperatures. A typical example of large complex circuitry may include a plurality of individual components and integrated circuits mounted on a "mother" board (typically a printed circuit board which physically and electrically integrates the components into a subsystem). When such circuitry is intended for military, aerospace or other critical end use, it is common to perform many tests thereon prior to assemblage into an overall system, including thermal checks to ensure operation at cold temperatures. Such circuitry may be interconnected with very complex test equipment, which performs series of tests, the results of which indicate probable causes for certain malfunctions, but which cannot isolate faults in all cases. In such cases, it has also been known to perform thermal checks on the circuitry while it is connected to test equipment, to see if the thermal checking will locate the fault. Although the phenomenon is not entirely understood, it is believed that one type of fault which is overcome through thermal checking is minor cracks in conductors which become reconnected when cooled to temperatures in the range of minus tens of degrees centigrade. In such cases, the temporary correction of the fault will provide an indication of proper operation within the test equipment, thus indicating a component or circuit area which is probably at fault. Further testing and/or replacement of components or portions of circuitry is then undertaken to cure the defect.

Heretofore, it has been common to use coolants which are generally referred to herein as chlorofluorocarbons (CFCs) of which there are a large number of varieties. A most common variety is dichlorodifluoromethane, which is also known as Freon 12 and Halon 22. The CFC is typically applied from an aerosol can (much like a hairspray can) which can be carried by workers in a tool pouch.

For some years, scientists have been concerned about the effects of CFCs on the atmosphere. First, CFC molecules themselves trap 20,000 times more heat than a molecule of carbon dioxide, thereby increasing the greenhouse effect far out of proportion to its concentration in air. More importantly, chlorine released when CFC molecules break up combines with and destroys ozone molecules. And each chlorine atom can eventually be re-released and combined with yet other ozone molecules so that their destructive effect is repetitive, perpetually. And, as is known, it is the ozone molecules which absorb most of the ultraviolet radiation from the sun, which is known to be extremely harmful to all forms of animal life, from humans down to the simplest of forms. For that reason, many governments of the world are now restricting, with the ultimate aim at totally banning, the production and use of CFCs.

Some attempts have been made to provide alternative methods of performing thermal checks on circuitry. Heat pumps have such minor cooling as to be unable to reach the desired temperatures (on the order of −30° to −60° C.) in even five or six minutes. Expansion of high pressure gases can produce temperatures as low as −30° C., but the high pressure gas causes physical damage to the circuitry under test. Thus far, no reasonable substitute seems to be available.

DISCLOSURE OF INVENTION

An object of the invention is to eliminate the need to use CFCs in thermal checking of electronic circuitry. Another object of the invention is to provide improved thermal checking of electronic circuitry.

According to the present invention, liquified nitrogen is sprayed directly on the surface of circuitry which is to be thermally checked.

In accordance with more specific aspects of the invention, the liquified nitrogen sprayed onto a surface in the process of thermal checking of integrated circuits contains a significant fraction of nitrogen in the liquid phase, which may be on the order of 30% to 90% liquid by molecular weight. Liquified nitrogen may be sprayed directly on surfaces of electronic circuitry with a relatively collimated stream (which may be less than a tenth of an inch in diameter), or in broad, fan-like sprays which may be on the order of ⅜ of an inch to an inch or more in length and one or a few tenths of an inch in width. According to the invention, the relative amount of nitrogen in the liquid phase being applied, the size (volume) of the stream, and the shape of the apertures can all be adjusted so as to best suit the particular needs of any thermal check to be performed.

The invention uses a gas which occurs in nature (not man-made), which is readily available throughout industry, and is therefore easy to obtain and inexpensive to use. The invention provides increased accuracy and discrimination in applying the coolant, reaches circuit-responsive temperatures more quickly, is totally inert to the atmosphere, and extremely safe for use by humans.

BEST MODE FOR CARRYING OUT THE INVENTION

Figure 1:
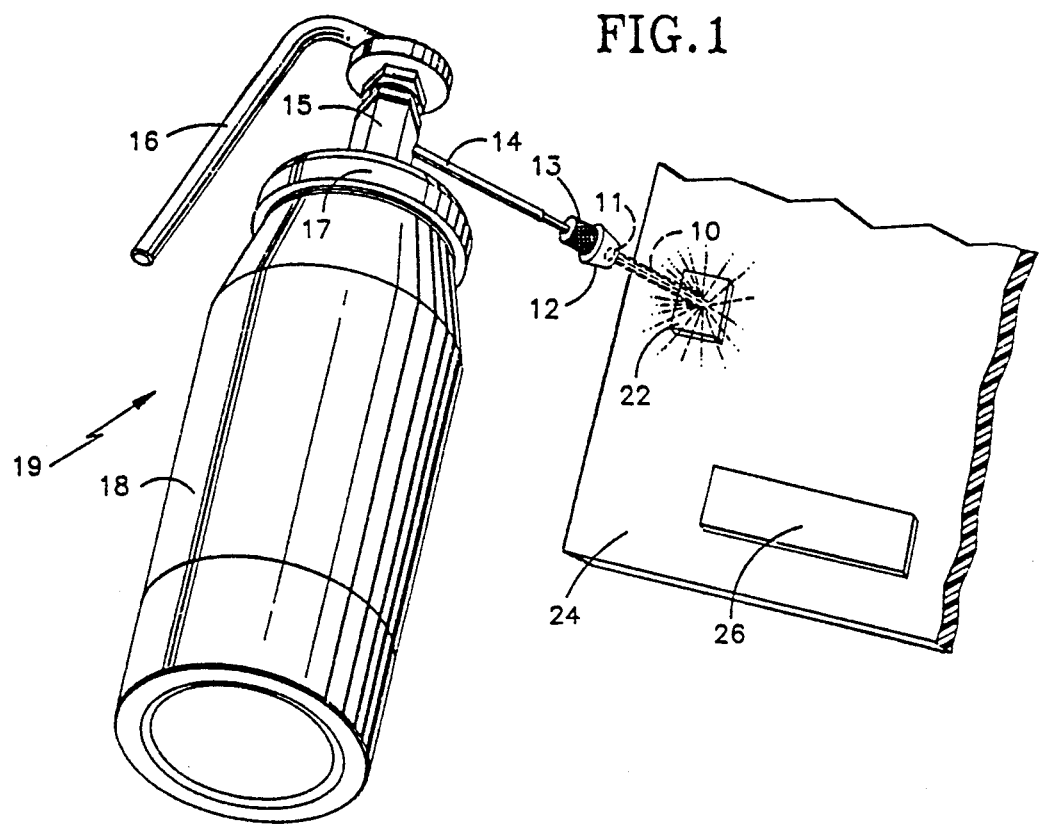
FIG. 1 is a simplified, perspective view of liquified nitrogen being sprayed directly on a component of an electronic circuit.

Referring now to FIG. 1, liquified nitrogen is propelled in a substantially collimated stream 10 from an aperture 11 formed in a tip 12 which may be threaded onto a fitting 13 of a delivery tube 14 from a valve 15 which is operated by a handle 16. The valve 15 is mounted on a cap 17 which in turn is threaded onto a dewar 18, with a feed pipe (not shown) extending from the valve 15 into the liquid within the dewar 18. The apparatus 11–18 comprises a cryogenic delivery unit 19 which may be of the type disclosed in U.S. Pat. No. 4,116,199 and 4,269,390. The dewar 18 is typically a double walled, stainless steel dewar having a high vacuum between the walls, so as to insulate the nitrogen contained therein from environmental heat. The dewar may be on the order of a third of a liter to a liter in capacity, although about ½ liter is found to be a good balance between weight and cumbersomeness (on the one hand) versus capacity, static holding time, and the like (on the other hand). The aperture 11 may range from about 20 mils (0.5 mm) to one the order of 50 mils (1.2 mm). The cryogenic delivery unit 19 may of course take a wide variety of forms, so long as it provides the practical application of a proper stream of liquified nitrogen through an aperture, having a substantial fraction of nitrogen in the liquid phase.

In FIG. 1, the nitrogen stream 10 is depicted as being propelled onto the surface of an electronic component 22 mounted on a circuit board 24. The circuit board 24 is also shown as having a much larger component 26 (which might be a complete integrated circuit, or otherwise) mounted thereon. The depiction in FIG. 1 is of course supersimplified, simply to illustrate the precepts of the present invention.

Figure 2:
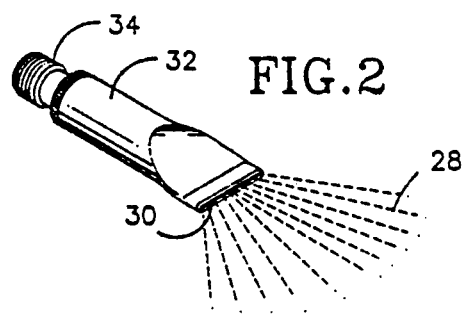
FIG. 2 is a perspective view of a broad, fan-like spray aperture.

For treating a much larger component (particularly one that is elongated such as the component 26 of FIG. 1), a broad, fan-like spray 28 may be utilized as shown in FIG. 2. The spray 28 is emerging from a relatively narrow, elongated aperture 30 which may be formed by carefully flattening one end of a tubular structure 32 which has a suitable fitting 34 to facilitate being fastened to the fitting 13 of the cryogenic delivery unit 19 (FIG. 1). Such a tube may be on the order of ¼ to ⅜ inch in diameter, yielding an aperture 30 having a length on the order of ½ to 1¼ inches, or the like. Depending on the volume of nitrogen which is capable of being delivered, much larger fan-like apertures 30 can be provided.

The analysis of liquified nitrogen as a coolant for thermal checking reveals some spectacular advantages in comparison with the use of CFCs.

The aerosol-type cans, utilized to spray CFCs on circuitry, produce a very broad, comb-like spray, which makes it impossible to confine the application thereof to specific small portions of a circuit. On the other hand, the characteristics of liquified nitrogen (which may have something to do with its high surface tension) allow delivering the liquified nitrogen in the form of a substantially collimated stream (that is, a parallel, non-diverging stream). Therefore, the application of the nitrogen can, in the extreme, be confined essentially to the diameter of the emerging stream, which is slightly more than the diameter of the nozzle aperture through which the stream is propelled. This can be as small as fractions of a millimeter.

CFCs tend to wet the surface, and tend to stand on the surface as evaporation occurs. The CFCs are also likely to be propelled along surfaces by the force of the propellant (whether the CFC is used as its own propellant or another propellant is used). Thus, a much larger surface than that which is desired to be tested is frequently wetted and cooled down by the CFCs. On the other hand, a stream of liquified nitrogen having a high liquid content has a tendency, when it impinges on the surface, to form a defined wetted surface area of liquid within which beads or droplets of liquid nitrogen are flowing radially outward and gasifying as they flow. The diameter of such a wetted area is relatively confined: for instance, a typical wetted area might be of a size on the order of a dime or a nickel. For small surfaces, the nitrogen stream, propelled radially outward from the point of impingement of the stream on the surface, will simply continue to propel outwardly, and vaporize into the atmosphere. On the other hand, the wetting characteristics of CFCs tend to cause them to flow around corners and wet other surfaces of the component.

Because CFCs have a maximum low temperature of −65° C. (and typically deliver the CFC to the surface at a higher temperature), it may take half a minute or more to cool an extremely small component (such as on the order of a quarter of an inch cube) sufficiently to cause the desired effect of locating the fault. On the other hand, the nitrogen can be delivered in the liquid phase, which is at −196° C., thus giving the capability for cooling components much more quickly. In fact, only on the order of 5 to 15 seconds is required for cooling most components using liquified nitrogen.

CFCs typically require the use of cardboard dams or other tools to tend to confine the CFCs to the portion which is desired to be cooled, thereby causing that portion to be cooled more quickly while at the same time avoiding cooling of other components. It is to be noted that the accuracy of which part of the circuitry is cooled, versus which part of the circuitry is not cooled, is very important in the diagnostic determination of where the fault lies. The more of the circuitry which is cooled, the less pinpointing there is of the precise area of defect.

The CFCs tend to splash around and frequently may impinge on the skin of an operator, particularly if he or she is using one hand to manipulate a tool or hold a unit in a particular relationship. The CFCs tend to adhere to, and wet, the skin and thereby cool it. A precaution required when utilizing liquid nitrogen is to avoid other than fleeting contact with the skin. Of course, in any given application of the present invention, simple precautions, such as gloves of any sort, can be utilized, if desired.

CFCs can react chemically with some of the materials which may be found in electronic circuits. On the other hand, nitrogen is known to be totally inert to any materials utilized in electronic circuitry.

CFCs are known to be toxic and a health hazard in the workplace. Effects on operators can include dizziness, involuntary trembling, unconsciousness, irregular heart beat, and even death. It has a greater tendency to promote frostbite on the skin or in the eyes. On the other hand, nitrogen (in any quantities which possibly could be utilized in the present invention) is totally innocuous and of no hazard whatsoever to humans (other than its heat extraction). All that occurs to humans is that the atmosphere (having approximately 89% nitrogen to begin with) has a slightly increased nitrogen content. In other than nearly total occlusion of the oxygen in an operator's environment, the nitrogen will not affect humans at all. And, as described hereinbefore, the characteristics of nitrogen as the liquid dances around and gasifies, render it even safer on the skin that CFCs.

CFCs are though to be relatively inexpensive however, the amount of nitrogen which is utilized in place of them, its general availability and the like, result in costs for the coolant itself which may range from 20% to 50% of the cost of the CFCs.

It has been known to use liquid nitrogen as the coolant for cryogenic high speed supercomputers. In such cases, the circuits are designed to be immersed in a liquified cryogen; the materials and other design factors are chosen so that such materials can all be chilled to the temperature of the cryogen without structural damage of alteration of the electronic phenomenon of the materials, other than the desired result of increased circuit speed. Immersion in cryogenic liquids is not practical for thermal checking of circuitry for several reasons: when initially immersed in the liquid, the warm circuitry structure will cause violent boiling (gasification) of the liquid nitrogen, the nitrogen gas tends to form an insulating sheath between the liquid and the surfaces of the structure, and thus precludes cooling the circuitry within a few seconds, as is required in thermal checking. And, naturally, cooling a substantial portion of a circuitry structure does not sufficiently pinpoint the fault as required in thermal checking.

Additionally, it is thought that extreme cooling (below $-100°$ C.) of a structure comprised of a variety of materials (epoxies, and the like) would tend to crystallize some of the materials, rendering them brittle and causing spontaneous cracking from shrinking. On the other hand, the use of a controlled, liquified nitrogen stream, as described herein, will cool an extremely small portion of a circuitry structure, usually being able to be confined to a surface of a single material, so that crystallization, brittleness and cracking can be avoided. Additionally, the desired temperature (of on the order of $-20°$ to $-60°$ C.) can be concentrated in a sufficiently small area so as to pinpoint the fault in a relatively short time.

As described in the embodiments of FIGS. 1 and 2, liquified nitrogen is propelled directly on a surface of the circuitry to be tested. At the present time, it is believed that such practice is to be preferred in most procedures which are now being performed with the use of CFCs. However, it is foreseen herein that with a broader application of liquified nitrogen in thermal checking processes, specific applications may be found which suggest the use of a closed probe to cool the circuitry under test.

The problem with a probe is that surface to surface contact is found to be less effective for thermal extraction from a surface than the direct application of the nitrogen as described hereinbefore with respect to FIGS. 1 and 2. This is believed to be due in part to the fact that such surfaces do not actually join molecularly, and therefore there are relatively lesser paths for heat flow from the surface to be cooled to the cooling surface. This is also believed to be due in part to the fact that the direct application of flowing liquid nitrogen across the surface has been found to be the most effective way to cool the surface. This is because of extracting heat of vaporization at the low boiling temperature rather than merely conducting heat into a mass at a low temperature. Another problem with probe tips is that it is extremely difficult to get the surface of the probe to conform well to the surface of the device being cooled, thereby to have maximum heat transfer therebetween. Therefore, it is believed that the use of liquified nitrogen properly applied directly to a surface to be cooled is to be preferred to use of probes.

The present invention has the additional advantage of nitrogen being inert to the materials, as well as being capable of application with a highly collimated stream. Thus, it can be used to cool surfaces which are not very accessible. In addition, if a circuit is connected with test equipment utilizing a lot of clips, probes and the like, the nitrogen can be applied through all of such connections either by means of an elongated delivery tube 14, or directly in the form of the collimated stream, because such collimated stream is so readily controlled.

Thus, although the invention has been shown and described with respect to exemplary embodiments thereof, it should be understood by those skilled in the art that the foregoing and various other changes, omissions and additions may be made therein and thereto without departing from the spirit and the scope of the invention.

I claim:

1. In a method of thermal checking electronic circuitry, the step of:
   propelling liquified nitrogen, having a significant fraction of said nitrogen in its liquid phase, directly onto a surface of the electronic circuitry to be thermally checked so as to extract heat from said circuitry at least partially as a result of some of said liquified nitrogen converting from liquid into gas at said surface.

2. The method according to claim 1 wherein said liquified nitrogen is between 30% and 90% liquid by molecular weight.

3. The method according to claim 1 wherein said liquified nitrogen is propelled through a small, circular aperture in the form of a substantially collimated stream.

4. The method according to claim 1 wherein said liquified nitrogen is propelled through an elongated aperture in the form of a flat, fan-shaped stream.

5. A method of checking multicomponent electronic circuitry in order to detect operational defects therein, said method comprising the steps of:
   a) placing said circuitry in an ambient temperature environment;
   b) connecting said circuitry to test equipment while said circuitry is in said ambient temperature environment;
   c) providing a supply of liquid nitrogen;
   d) spraying liquid nitrogen from said supply thereof directly onto selected components of said circuitry so as to cryogenically cool said selected components at least partially as a result of some of said liquid nitrogen converting from liquid into gas on said selected components; and
   e) noting any malfunctions indicated by the results of said cooling step.

6. The method of claim 5 wherein said spraying step directs a spray against said selected components which said spray has a liquid nitrogen content in the range of about 30% to about 90% by molecular weight.

7. The method of claim 5 wherein said spraying step comprises spraying said liquid nitrogen through a small circular aperture in a substantially collimated stream.

8. The method of claim 5 wherein said spraying step comprises spraying said liquid nitrogen through an elongated aperture in a flat fan-shaped stream.

9. A method for checking multicomponent electronic circuitry in order to detect operational defects therein, said method comprising the steps of:
   a) placing said circuitry in an ambient temperature environment;
   b) connecting test equipment to said circuitry while the latter is in said ambient temperature environment;
   c) providing a supply of liquid nitrogen;
   d) spraying a stream composed of 30% to 90% of liquid nitrogen by molecular weight from said supply of liquid nitrogen directly onto selected components of said circuitry so as to cryogenically cool said selected components at least partially as a result of some of said liquid nitrogen converting from liquid into gas on said selected components; and e) noting any malfunctions which are the results of said cooling step, and which indicate fault in said components.

10. The method of claim 9 wherein said stream is a substantially collimated stream.

11. The method of claim 9 wherein said stream is a flat fan-shaped stream.

* * * * *

UNITED STATES PATENT AND TRADEMARK OFFICE
CERTIFICATE OF CORRECTION

PATENT NO. : 5,222,999

DATED : Jun. 29, 1993

INVENTOR(S) : Michael D. Bryne

It is certified that error appears in the above-identified patent and that said Letters Patent is hereby corrected as shown below:

Column 3, line 6, "one" should be --on--.

Column 4, line 57, "though" should be --thought--;
        line 57, "inexpensive" should be --inexpensive;--; and
        line 68, "of" should be --or--.

Signed and Sealed this

First Day of February, 1994

*Attest:*

BRUCE LEHMAN

*Attesting Officer*      *Commissioner of Patents and Trademarks*